United States Patent
Watanabe

(10) Patent No.: US 6,364,664 B1
(45) Date of Patent: Apr. 2, 2002

(54) DENTAL IMPLANT PARTS

(75) Inventor: Kiyoshi Watanabe, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/614,165

(22) Filed: Jul. 11, 2000

(30) Foreign Application Priority Data

Jul. 12, 1999 (JP) .......................................... 11-197509

(51) Int. Cl.[7] .................................................. A61C 8/00
(52) U.S. Cl. ...................................... 433/174; 433/173
(58) Field of Search ................................ 433/172, 173, 433/174, 175, 176, 141

(56) References Cited

U.S. PATENT DOCUMENTS

| | | | |
|---|---|---|---|
| 5,562,447 A | | 10/1996 | Moy et al. ................... 433/150 |
| 5,569,037 A | | 10/1996 | Moy et al. ................... 433/173 |
| 5,577,871 A | * | 11/1996 | Brugola ....................... 411/404 |
| 5,810,590 A | * | 9/1998 | Fried et al. .................. 433/172 |
| 5,863,200 A | | 1/1999 | Hamada et al. ............. 433/173 |

* cited by examiner

Primary Examiner—John J. Wilson
(74) Attorney, Agent, or Firm—Oblon, Spivak, McClelland, Maier & Neustadt, P.C.

(57) ABSTRACT

A dental implant including an engagement portion provided in a head portion to be engaged with an engagement member to rotate the parts, wherein the engagement portion is a hole having a lateral cross-sectional shape of double squares in which two squares with the same shape having a common central axis are superimposed at a relative angle of from 20° to 45°. By use of the dental implant, even when an engagement portion provided in a head portion to be engaged with an engagement member to rotate the parts is partly damaged by an excessive torque or the like at the time of operation once effected, it is possible to fasten again the parts with the screw and release the parts from the screw, and the operability during engagement with the engagement member is good.

6 Claims, 3 Drawing Sheets

DENTAL IMPLANT PARTS

BACKGROUND OF THE INVENTION

1. Field of the Invention

The present invention relates to a dental implant parts in which, even when an engagement portion provided in a head portion to be engaged with an engagement member to rotate the parts is partly damaged by an excessive torque or the like at the time of operation once effected, it is possible to again fasten the parts with a screw or release the parts from the screw, and the operability is good.

2. Conventional Art

As dental prosthetic methods in a missing tooth portion, there have hitherto been generally employed a method by using a bridge and a method by using a partial denture.

According to the method by using a bridge, healthy natural teeth at the both sides of a missing tooth portion are cut to form abutment teeth, and between metallic bodies to be engaged with and fixed to the abutment teeth, a dental prosthesis positioned in the missing tooth portion is fixed. Therefore, this method involves such defects that not only the healthy natural teeth must be cut in order to form the abutment teeth, but also since an occlusion stress is not directly applied to the abutment teeth portion, bone resorption is caused in the subjected site.

Further, according to the method by using a partial denture, one prepared by fixing an artificial tooth to a denture base made of a synthetic resin, etc. is a dental prosthesis. However, in this method, an occlusal force applied to the dental prosthesis is burdened by remaining natural teeth adjacent to the partial denture and/or an oral mucosa. Thus, one may have a sense of incongruity during use of the dental prosthesis, or the denture base may cover gustatory organs exsisted in an oral mucosa tissue to cause torpor of the taste. Moreover, this method involves a serious defect that the use over a long period of time may likely cause alveolar bone resorption.

Thus, as a remedy method for overcoming these defects, there has been developed and practiced a technique of dental implant in which an implant fixture as a retaining and stabilizing device for dental prosthesis is implanted into an implantation hole formed in a maxillary bone of a missing tooth portion and made act for a function of a tooth root in a natural tooth, a fixing device for dental prosthesis is fixed to an abutment fixed in the oral side of the implant fixture to act as a retainer for dental prosthesis, and a dental prosthesis is fixed to the fixing device for dental prosthesis.

In practicing this remedy method by using a dental implant, the dental prosthesis can be fixed without covering an oral mucosa Therefore, at the time of setting the dental prosthesis, neither sense of incongruity nor torpor of the taste is caused. Further, a feeling of use similar to one of using a natural too this obtained Moreover, there is an advantage that since the maxillary bone is imparted with a proper occlusal force, the bone resorption assumed in the case that no implant fixture is implanted can be kept to a minimum. Accordingly, this remedy method has been rapidly developed and applied to not only single tooth deficiency or partial deficiency of two or more teeth but also edentulous jaw (all missing teeth).

As the remedy method by using a dental implant, there is mainly employed a double technique in which, not only the implant fixture implanted in the implantation hole formed in the maxillary bone in the missing tooth portion has been thoroughly bound to the maxillary bone in the missing tooth portion, but also an operated portion by the formation of the implantation hole has been cured, and then a gingival portion in the oral side at which the implant fixture is implanted is again incised, and an abutment acting as a fixing portion of the fixing device for dental prosthesis is fixed to the oral side portion of the implant fixture.

In the remedy method by using a dental implant according to the double technique, the first-stage remedy is carried out in the following manner. That is, a gingiva of a portion of the missing tooth portion in which the implant fixture is to be implanted is cut open to form a gingival flap; an implantation hole for implant fixture is formed in an alveolar bone of the exposed maxillary bone; the implant fixture is implanted in the implantation hole; a female screw opened in the oral side of the implanted implant fixture is engaged with a male screw of an implant cover screw, an end portion in the implant fixture side of which has an external size equal to or larger than an approximately columnar end portion in the oral side of the implant fixture, and which has a truncated cone shape such that the outer diameter increases as it is away from the implant fixture, and a surface in the implant fixture side of which is provided with a concave capable of accommodating a rectangular cylinder portion protruded in an end portion positioned in the oral side of the implant fixture and with the male screw in a central portion thereof, thereby sealing the female screw opened in the oral side of the implant fixture and preventing the bone to grow to the oral side from the implant fixture during the remedy stage; the gingival flap is returned to the original state to cover the alveolar bone of the exposed maxillary bone by the gingival flap; and the gingival flap is then sutured at the cut position.

The second-stage remedy is carried out as follows. That is, after the implant fixture implanted in the implantation hole formed in the maxillary bone in the missing tooth portion has gained an osseous joint in the implantation hole (usually, this period is from about 3 to 6 months), the gingiva is cut open in the portion of the alveolar bone implanted with the implant fixture to form a gingival flap, thereby exposing the implant cover screw; the implant cover screw engaged with the implant fixture is removed; the female screw opened in the oral side of the implant fixture is engaged with a male screw of a healing abutment, an end portion in the implant fixture side of which has an external size approximately equal to an approximately columnar end portion in the oral side of the implant fixture and a length longer than the thickness of the circumferential gingiva, and the implant fixture side of which has a shape substantially the same as in the abutment, and a surface in the implant fixture side of which is provided with a concave capable of accommodating the rectangular cylinder portion protruded in the end portion positioned in the oral side of the implant fixture and with the male screw in a central portion thereof, thereby sealing the female screw opened in the oral side of the implant fixture; the gingival flap is returned to the original state to cover the alveolar bone of the exposed maxillary bone by the gingival flap, while exposing the head side of the healing abutment; and the gingival flap is then sutured at the cut position.

The second-stage remedy is generally completed within about two weeks. In this case, since the gingiva is in the state of coming into contact with the implant fixture side of the healing abutment, the healing abutment is removed in this state, whereby the remedy by using a dental implant is completed. FIG. 5 is a longitudinal cross-sectional view showing the state after completion of the dental implant remedy. In FIG. 5, in the oral side of the implant fixture 1, is aligned the abutment 2, the side of the implant fixture 1 of which has a shape approximately the same to the side of the implant fixture 1 of the healing abutment; and an abutment screw 3 is engaged in a female screw of the implant fixture 1 through the abutment 2, to fix the abutment 2 to the oral side of the implant fixture 1. And, in the case that a gold cylinder 5 provided with the dental prosthesis 6 on an outer surface thereof is expected to be completed, a male screw of a healing cap for sealing a through-hole opened in the oral side of the abutment 2 is screwed into a female screw provided in the oral side of the abutment screw 3; after the gold cylinder 5 provided with the dental prosthesis 6 on the outer surface thereof has been completed, the healing cap is removed; the gold cylinder 5 provided with the dental prosthesis 6 on the outer surface thereof is aligned in the oral side of the abutment 2; a gold screw 4 is screwed into a female screw provided in the abutment screw 3 or the abutment 2 through the dental prosthesis 6 and the gold cylinder 5, to fix the dental prosthesis 6 to the oral side of the implant fixture 1 via the abutment 2; and a through-hole of the dental prosthesis 6 allowing the gold screw 4 to pass through is sealed in the oral side thereof with a dental composite resin 7 or the like, whereby the remedy by using a dental implant is completed.

In the remedy by using a dental implant, a number of implant parts are used. In order to fix each parts, a screw is used. In a head portion of implant parts (such as an implant cover screw, a healing abutment, an abutment screw, a healing cap, and a gold screw) provided with a male screw to enable the parts to be screwed into a female screw, an engagement portion to be engaged with an engagement member for rotating the parts, such as a screwdriver or a rod spanner, is formed.

The implant parts is a very small parts used in a narrow portion in the oral cavity, there are used many parts, a head portion of each of which comes into other parts and it is disliked that angular portions are present in the portions exposed to the oral side. Therefore, in the engagements portion to be engaged with the engagement member including a screwdriver or a rod spanner, formed in the head portion of the dental implant parts provided with a male screw, portions having an outer shape such as a hexagon and a quadrangle, as in usual parts including bolts, cannot be provided, but those provided with a slotted head, a cross recessed head, a hexagonal socket, a square socket, etc. are used. And, screw fastening was carried out by means of an engagement member, a tip portion of which is provided with a portion having a shape to be engaged with the respective engagement portion, such as a screwdriver or a rod spanner (hexgon socket key etc.).

However, in the case that the engagement portion is of a slotted head, i.e., it is fastened by an engagement member such as a screwdriver, when the slot has been once damaged by an excessive torque, it is impossible to undergo normal rotation although reverse rotation is possible. Further, since it is impossible to retain the dental implant parts only by the engagement member, the operability is inferior.

In contrast, in the case that the engagement portion is of a cross recessed head, i.e., it is fastened by an engagement member such as a screwdriver for cross recessed head, as compared with the case that the engagement portion is of a slotted head, the engagement between the engagement portion and the engagement member is easy, and the operability is good. Further, it is possible to retain the dental implant parts by the engagement member to a certain extent. However, when the cross recessed head has been once damaged by an excessive torque, since the damaged portion becomes a cardinal point in a center side of the cross recess, it is impossible to undergo rotation to any of the normal and reverse directions.

Further, in the case that the engagement portion is of a hexagonal socket, i.e., it is fastened by an engagement member such as a hexagonal socket key, such is widely admired because it is possible to retain the dental implant parts by the engagement member. However, when the hexagonal socket has been once damaged by an excessive torque, since the lateral cross-sectional shape of the hexagonal socket becomes a shape close to a circle due to the damage, it is impossible to undergo rotation to any of the normal and reverse directions.

In contrast, in the case that the engagement portion is of a square socket, i.e., it is fastened by an engagement member such as a square socket key, since such is inferior in the operability in engagement with the engagement member to the case of the hexagonal socket due to the symmetric property, its range for use is restricted. However, it is possible to retain the dental implant parts by the engagement member, and even when the hole has been damaged, its lateral cross-sectional shape does not become a circle unlike the case of the hexagonal socket. Accordingly, it has an advantage that even in the case that it is damaged by an excessive torque or the like, it is possible to undergo rotation at least to the reverse direction.

As described above, at present, there is no engagement portion which can meet various requirements that when a groove (such as slot, cross recess) or a hole (such as the socket) is partly damaged, it is possible to undergo rotation to both of the normal and reverse directions, a dental implant parts can be retained by an engagement member such as a screwdriver or a rod spanner, and that the operability during engagement with an engagement member is good.

On the other hand, since a dental implant parts provided with a male screw is required to have bioaffinity, it is made of titanium or a titanium alloy, or of a material such as a gold alloy, and hence, its strength is comparatively weak. Further, since it is small in size, not only a portion to be engaged with an engagement member such as a screwdriver or a rod spanner is small in size, but also a phenomenon in which the engagement portion is damaged is liable to occur. When the engagement portion has been damaged, the parts cannot be removed after being fixed to a human body. As a result, other parts cannot be removed, too, leading to a fatal defect that neither repair nor other remedy can be made. Thus, it has been highly demanded to solve this defect.

SUMMARY OF THE INVENTION

The present invention is aimed to provide a dental implant parts which can overcome the defect of the conventional art dental implant parts as described above (i.e., when an engagement portion provided in a head portion thereof is partly damaged by an excessive torque or the like at the operation once effected, it is impossible to undergo at least fastening the parts again with a screw), in which, even when an engagement portion provided in a head portion thereof is partly damaged by an excessive torque or the like at the operation once effected, it is possible to fasten the parts again with a screw or release the parts from the screw, and the operability during engagement with an engagement member for rotating the parts is good.

In order to attain the above-described aim, we, the present inventors made extensive and intensive research. And, among the conventional art engagement portions including those of a slot, cross recess, a hexagonal socket, and a square socket, made research on the case of a square hole which has advantages such that it is possible to retain the dental implant parts by an engagement member such as a rod spanner and that even when it has been broken by an excessive torque or the like, it is possible to undergo rotation at least to the reverse direction. As a result, it has been found that the above-described aim can be attained by a dental implant parts including an engagement portion provided in a head portion to be engaged with an engagement member to rotate the parts, wherein the engagement portion is a hole having a lateral cross-sectional shape of double squares in which two squares with the same shape having a common central axis are superimposed at a relative angle of from 20° to 45°.

A more complete appreciation of the present invention, and many of the attendant advantages thereof, will be more readily obtained as the same becomes better understood by reference to the following detailed description when considered in connection with the accompanying drawings, wherein:

DESCRIPTION OF THE PREFERRED EMBODIMENTS

Embodiments of the dental implant parts according to the present invention will be hereunder described in detail with reference to the drawings.

Figure 1:
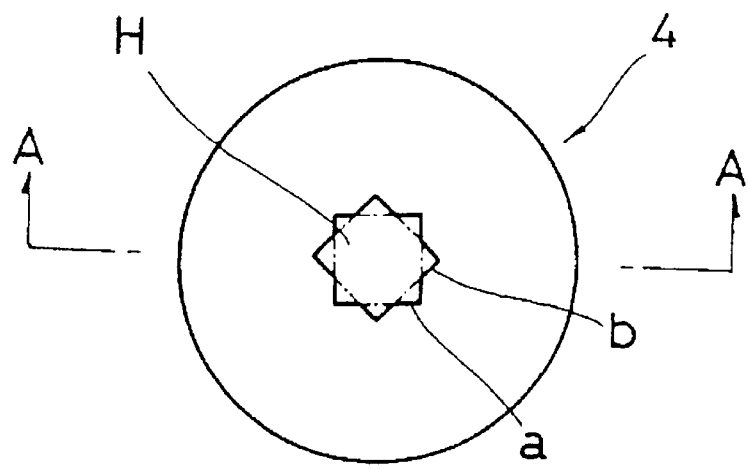
FIG. 1 is a planar enlarged view to show one embodiment of a gold screw as a dental implant parts according to the present invention, in which an engagement portion provided in a head portion thereof is a hole having a lateral cross-sectional shape of double squares in which two squares with the same shape having a common central axis are superimposed at a relative angle of 45°.
Figure 2:
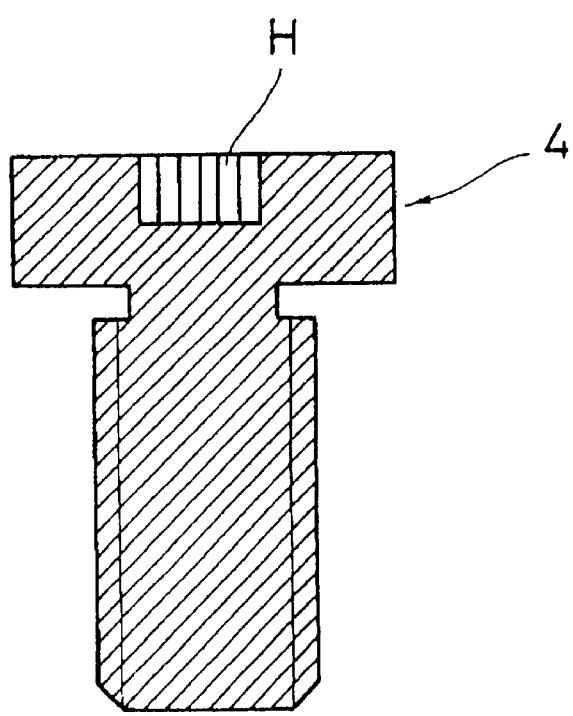
FIG. 2 is an A—A line cross-sectional view of FIG. 1.
Figure 3:
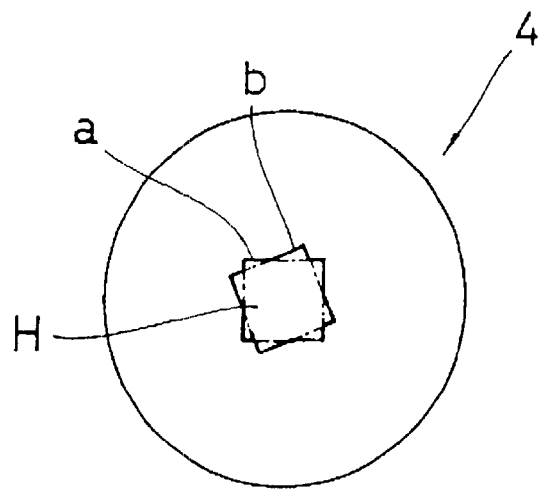
FIG. 3 is a planar enlarged view to show one embodiment of a gold screw as a dental implant parts according to the present invention, in which an engagement portion provided in a head portion thereof is a hole having a lateral cross-sectional shape of double squares in which two squares with the same shape having a common central axis are superimposed at a relative angle of 20°.

FIG. 1 is a planar enlarged view to show one embodiment of a gold screw as a dental implant parts according to the present invention, in which an engagement portion provided in a head portion thereof is a hole having a lateral cross-sectional shape of double squares in which two squares with the same shape having a common central axis are superimposed at a relative angle of 45°; FIG. 2 is an A—A line cross-sectional view of FIG. 1; FIG. 3 is a planar enlarged view to show one embodiment of a gold screw as a dental implant parts according to the present invention, in which an engagement portion provided in a head portion thereof is a hole having a lateral cross-sectional shape of double squares in which two squares with the same shape having a common central axis are superimposed at a relative angle of 20°; and FIG. 4 is a view to show the state in which the engagement portion shown in FIG. 1 is broken.

Figure 5:
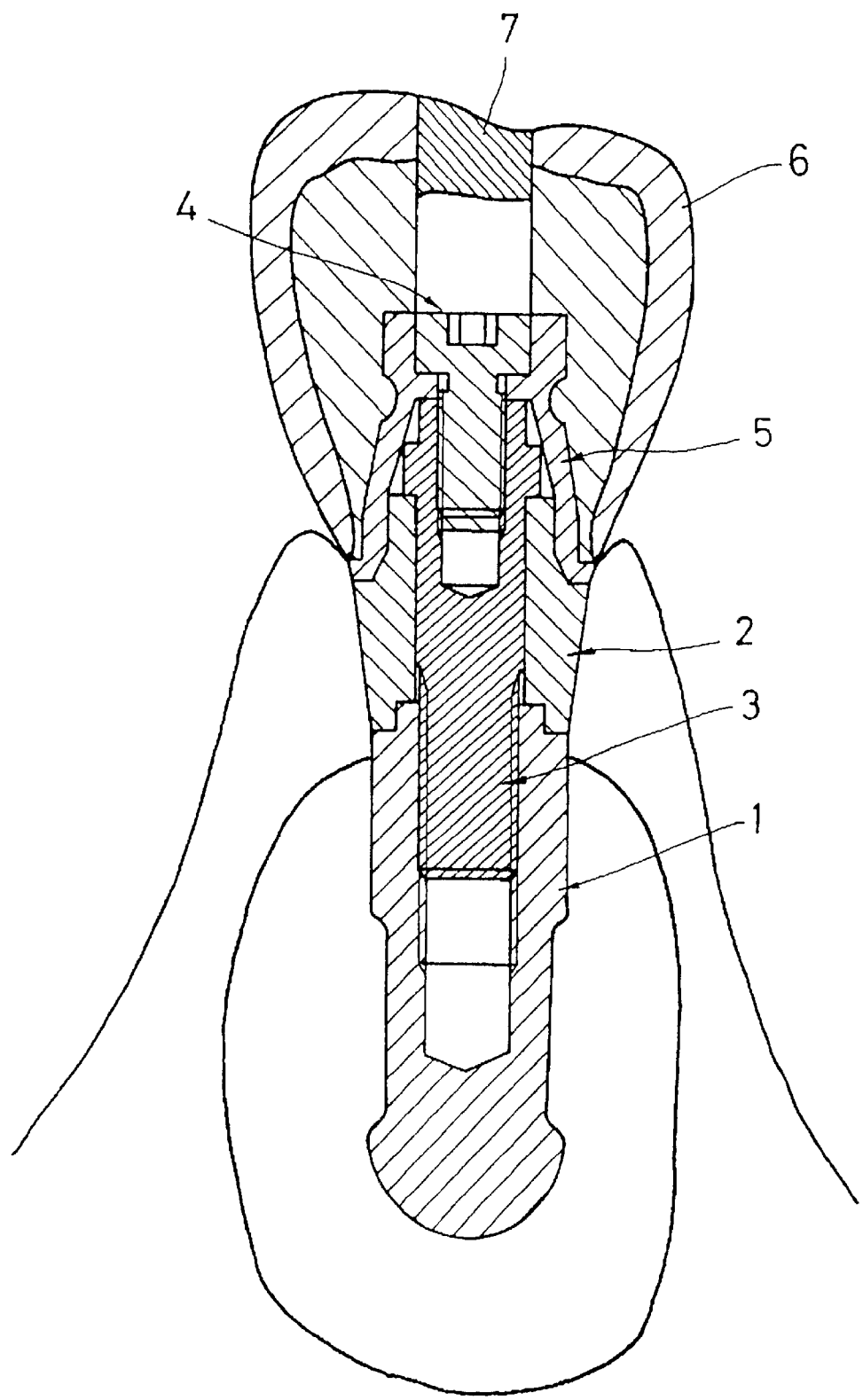
FIG. 5 is a longitudinal cross-sectional view to show the state after completion of the dental implant remedy.

In the drawings, a numeral 4 is a gold screw as a dental implant parts according to the present invention. As shown in FIG. 5, the gold screw 4 passes through an abutment 2 aligned in an oral side of an implant fixture 1 and engages an abutment screw 3 in a female screw of the implant fixture 1 to fix the abutment 2 in the oral side of the implant fixture 1. Then, a gold cylinder 5 provided with a dental prosthesis 6 on an outer surface thereof is aligned in the oral side of the abutment 2, and the gold screw 4 passes through the dental prosthesis 6 and the gold cylinder 5 and is engaged in a female screw provided in the abutment screw 3 or the abutment 2 (the abutment screw 3 in the embodiment as shown in FIG. 5), to fix the dental prosthesis 6 to the oral side of the implant fixture 1 via the abutment 2. An engagement portion provided in a head portion of the gold screw 4 is formed into a hole H having a lateral cross-sectional shape of double squares in which two squares a, b with the same shape having a common central axis are superimposed at a relative angle of from 20° to 45°.

When the gold screw 4 as a dental implant parts having an engagement portion of such a structure passes through the dental prosthesis 6 and the gold cylinder 5 and is rotated and engaged in the female screw provided in the abutment screw 3 or the abutment 2 (the abutment screw 3 in the embodiment as shown in FIG. 5), to fix the dental prosthesis 6 to tile oral side of the implant fixture 1 via the abutment 2, the gold screw 4 is inserted into a through-hole provided through the dental prosthesis 6 and the gold cylinder 5; an engagement member such as a square rod spanner is engaged in the hole H as the engagement portion provided in the head portion of the gold screw 4; and the gold screw 4 is rotated and engaged in the female screw provided in the abutment screw 3 or the abutment 2 (the abutment screw 3 in the embodiment as shown in FIG. 5). In this case, since the hole H as the engagement portion is formed in a lateral cross-sectional hole shape in which two squares a, b with the same shape having a common central axis are superimposed at a prescribed relative angle, in the engagement with the engagement member, the engagement member may be rotated so as to engage with either one of the squares a, b. Therefore, as compared with the case that the hole as the engagement portion is a single square hole, a rotation angle of the engagement member may be made small, so that the operability is good.

Figure 4:
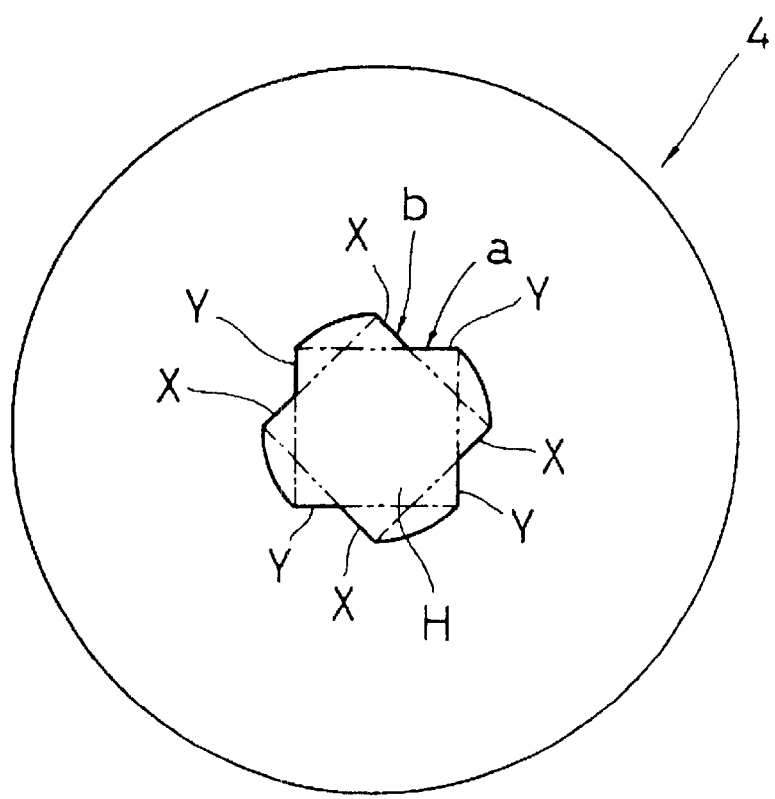
FIG. 4 is a view to show the state in which the engagement portion shown in FIG. 1 is broken.

And, even in the case that the engagement portion provided in the head portion of the dental implant parts is partly damaged by a torque or the like at the time of operation once effected, as shown in FIG. 4 (the normal rotation side of the square a), a portion X of the square b contributing to the normal rotation and a portion Y of the square a contributing to the reverse rotation remain without being damaged, and hence, it is possible to undergo fastening with the screw or release from the screw.

The reasons why the engagement portion must be formed into the hole H having a lateral cross-sectional shape of double squares in which two squares a, b with the same shape having a common central axis are superimposed at a relative angle of from 20° to 45° are as follows, That is, since the lateral cross-sectional shape of the hole H is of double squares in which two squares with the same shape having a common central axis are superimposed at a relative angle, the relative angle which could be taken is within a range of from 0° to 45°. If the relative angle is less than 20°, a phenomenon in which the connecting portions of the two squares are broken at the same time by the breakage of the double square hole occurs, whereby a phenomenon likely occurs, in which rotation to any of the normal and reverse directions cannot be no more effected. Thus, such is not preferred. Further, an upper limit of the relative angle is 45° from the standpoint of the symmetric property of the figure.

As described above in detail, the present invention gives rise to the following effects. Since dental implant parts including an engagement portion provided in a head portion are required to have bioaffinity, it is made of titanium or a titanium alloy, or of a material such as a gold alloy, and hence, its strength is comparatively weak; since it is small in size, not only is a portion to be engaged with an engagement member such as a screwdriver or a rod spanner small in size, but also a phenomenon in which the engagement portion is damaged is liable to occur; and when the engagement portion has been damaged, the parts cannot be taken out after being fixed to a human body, leading to a fatal defect that neither repair nor other remedy can be made. In this regard, according to the present invention, the engagement portion is a hole having a lateral cross-sectional shape of double squares in which two squares with the same shape having a common central axis are superimposed at a relative angle of 20° to 45°. Thus, even when the engagement portion is partly damaged by an excessive torque or the like at the operation once effected, since in the two squares having the same shape, the respective portions to be engaged with the engagement portion remain, it is possible to fasten again the parts with the screw and release the parts from the screw, and the operability during engagement with the engagement member is good.

In the light of the above, the value of the dental implant parts according to the present invention in contributing to the dental field, particularly in the dental implant remedy field is very high.

While the invention has been described in detail and with reference to specific embodiments thereof, it will be apparent to one skilled in the art that various changes and modifications can be made therein without departing from the spirit and scope thereof.

What is claimed is:

1. A dental implant comprising:
   a head portion;
   an engagement portion provided in the head portion, wherein the engagement portion is a hole having a lateral cross-sectional shape of double squares in which two squares with the same shape having a common central axis are superimposed at a relative angle of from 20° to 45°.

2. The dental implant parts according to claim 1, wherein said engagement portion is made of a gold alloy.

3. The dental implant parts according to claim 1, wherein said engagement portion is made of a titanium alloy.

4. A dental implant comprising:
   an implant fixture;
   a screw inserted in the implant fixture, the screw including:
      a head portion;
      an engagement portion provided in the head portion, wherein the engagement portion is a hole having a lateral cross-sectional shape of double squares in which two squares with the same shape having a common central axis are superimposed at a relative angle of from 20° to 45°.

5. The dental implant parts according to claim 4, wherein said engagement portion is made of a gold alloy.

6. The dental implant parts according to claim 4, wherein said engagement portion is made of a titanium alloy.

* * * * *